United States Patent [19]

Lyman et al.

[11] 4,349,632

[45] Sep. 14, 1982

[54] TISSUE CULTURE CLUSTER DISH

[75] Inventors: George F. Lyman, Rocky Point, Me.; Alan Lowry, Canton, Mass.

[73] Assignee: Data Packaging Corporation, Cambridge, Mass.

[21] Appl. No.: 244,731

[22] Filed: Mar. 17, 1981

[51] Int. Cl.³ .............................................. C12M 3/00
[52] U.S. Cl. ................................. 435/284; 206/45.18; 217/58; 220/335
[58] Field of Search ............... 435/284, 285, 286, 297, 435/298, 299, 300, 301; 220/335; 206/45.18; 217/58

[56] References Cited

U.S. PATENT DOCUMENTS

| | | | |
|---|---|---|---|
| 3,240,375 | 3/1966 | Burrows | 220/335 X |
| 3,597,326 | 8/1971 | Liner | 435/301 X |
| 3,632,478 | 11/1968 | Fink | 435/301 |
| 3,728,228 | 4/1973 | Duranty | 435/301 |
| 3,850,342 | 11/1974 | Dsjuba | 220/335 X |
| 4,012,288 | 3/1977 | Lyman et al. | 435/284 |
| 4,038,149 | 7/1977 | Liner et al. | 435/300 |

Primary Examiner—Robert J. Warden
Attorney, Agent, or Firm—Wolf, Greenfield & Sacks

[57] ABSTRACT

A tissue culture cluster dish having a multi-well base and detached cover. The cover may be ounted on the base in a partially open position to provide access to the wells by a pipette or other instrument operated by the user while the cover acts as a shield against airborne contaminants.

10 Claims, 9 Drawing Figures

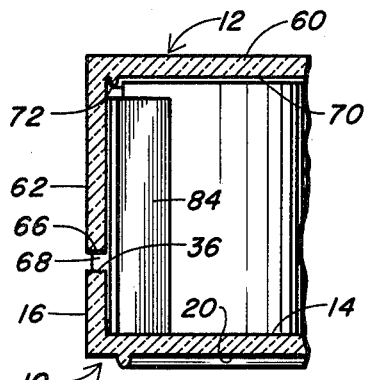
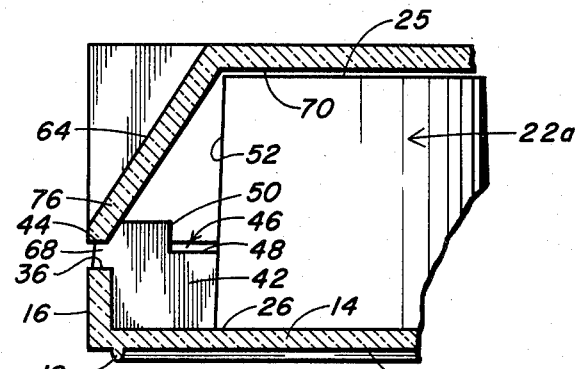
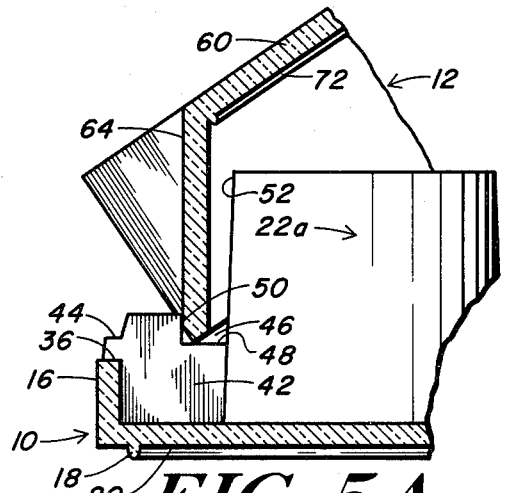
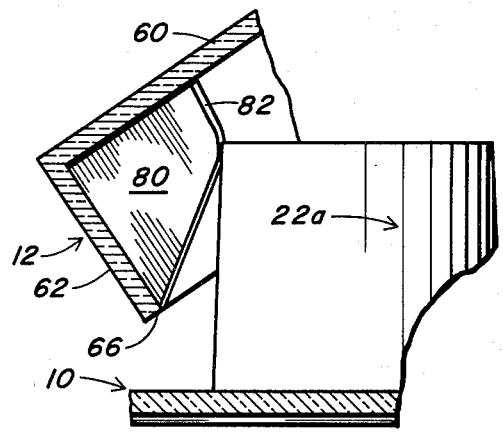
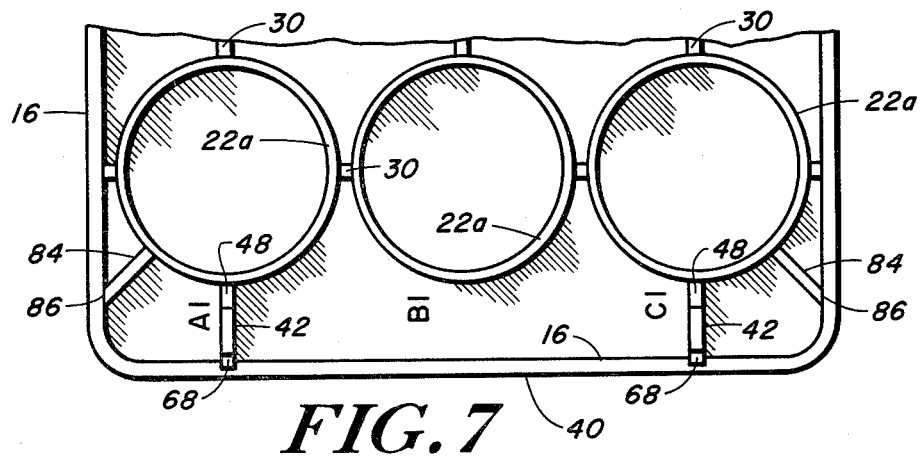

TISSUE CULTURE CLUSTER DISH

INTRODUCTION

The present invention relates to tissue culture dishes and more particularly comprises a new and improved multi-well tissue culture dish which is particularly convenient to use in the laboratory. The cluster dish of the present invention is an improvement over the multi-well dish shown in U.S. Pat. No. 4,012,288 having a common assignee with the present application.

The present invention may be embodied in multi-well culture dishes having different numbers of wells. Typically, the invention may be embodied in 12 and 24 well cluster dishes. The tissue cluster dishes now on the market have covers that are designed to be placed in only one position on the base, namely, in a position wherein the several wells in the base are closed by the cover so as to prohibit access by a pipette or other instrument to the wells, except that the cover and base are designed to allow atmospheric communication with the interior of the wells. When reagents are to be added to the wells in those dishes, the investigator must either remove the cover (and place in on some convenient surface), or if he chooses to use the cover as a shield so as to prevent contamination from airborne substances, he will try to hold the base and cover with the cover elevated above the dish but in a position to prevent contaminants from falling in the wells. This is a rather awkward manipulation and the investigator runs some risk of dropping or spilling the dish.

The principal object of the present invention is to provide a cluster dish having a cover that is designed to be seated in either one of two positions on the base. In the first position, the cover performs its normal function of closing the wells except for enabling the wells to assume the atmospheric conditions of the ambient atmosphere. In the second position, the cover is supported above the dish at an angle thereto, which exposes the wells sufficiently so that the investigator may reach the wells with a pipette but at the same time provides a roof over the dish so as to prevent airborne contaminants from reaching the wells. The cover is so supported that the investigator need not separately hold it in position but rather the investigator need only support the base of the dish itself as the base carries the cover.

These and other objects and features of this invention will be better understood and appreciated from the following detailed description of two embodiments thereof, selected for purposes of illustration and shown in the accompanying drawing.

BRIEF DESCRIPTION OF THE DRAWINGS

FIG. 4 is a fragmentary cross sectional view of the dish taken along section line 4—4 of FIG. 2 and showing the cover in the closed position;

FIGS. 5 and 5A are fragmentary cross sectional views of the dish taken along section line 5—5 of FIG. 3 and showing the cover in the closed and partially open positions, respectively;

FIG. 6 is a fragmentary cross sectional view of the dish taken along section line 6—6 of FIG. 3 and showing the cover in the partially open position;

FIG. 7 is a fragmentary top plan view of the rear end of the base of the dish.

DETAILED DESCRIPTION OF THE DRAWINGS

Figure 1:
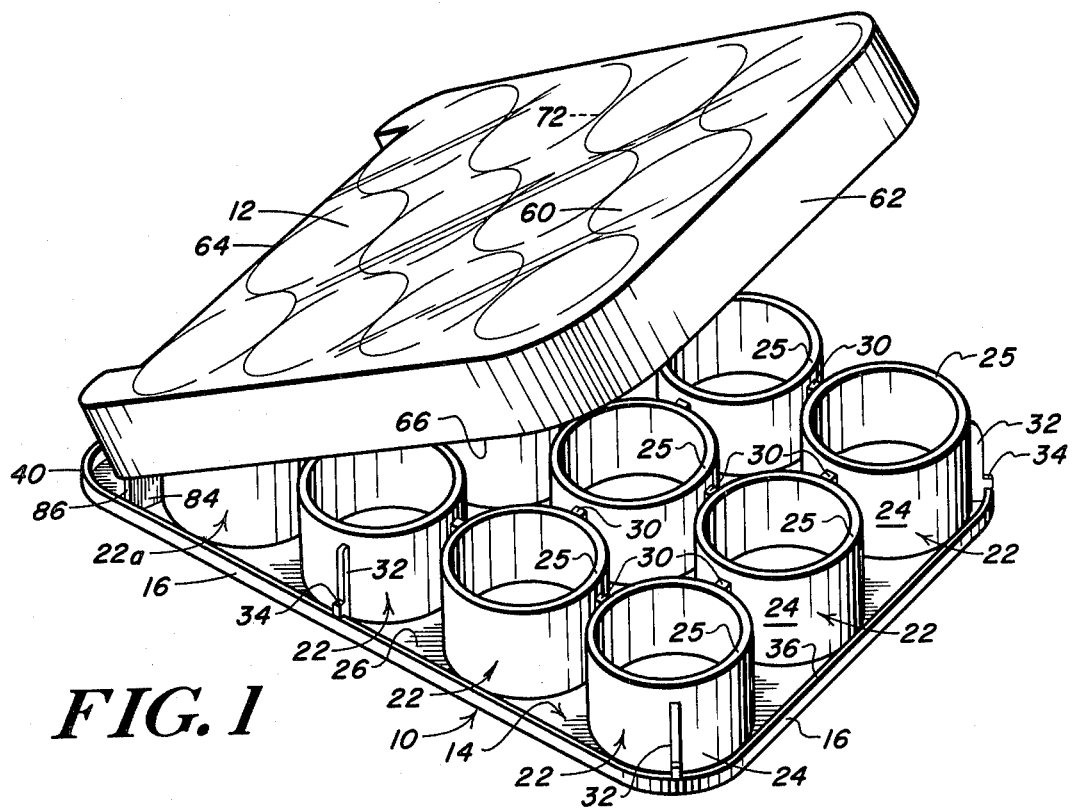
FIG. 1 is a perspective view of one embodiment of a tissue culture cluster dish constructed in accordance with this invention, with the cover shown mounted in its partially open position on the base.
Figure 2:
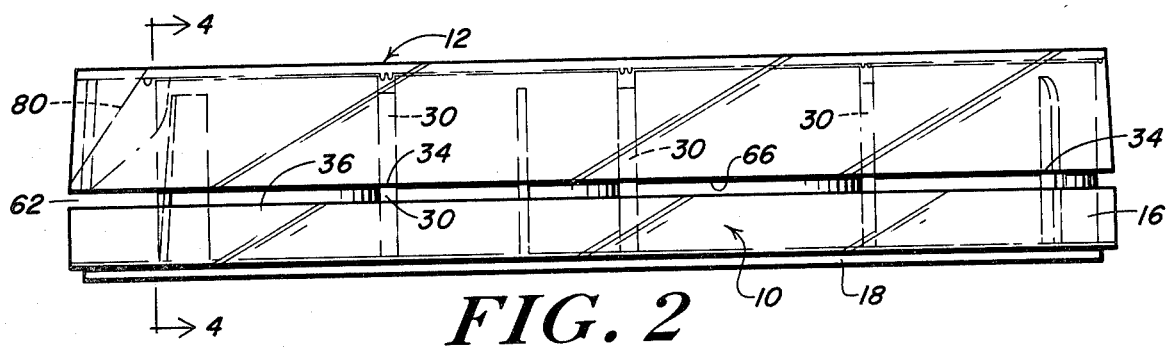
FIG. 2 is a side view of the cluster dish of FIG. 1 but showing the cover in its closed position.

The tissue culture plate shown in FIGS. 1-7 includes a base 10 and cover 12. The cover 12 may be completely removed from the base 10 so as to completely expose the base, and alternatively, the cover may be mounted on the base in either of two positions. In FIG. 1 the cover is shown mounted in a tilted position on the base so as to expose the wells 22 on the base so that a reagent may be introduced to them, or the cover may be placed in a closed position on the base which essentially prohibits access to the wells. The cover is shown in the closed position in FIG. 2. The cover in the closed position is supported slightly above the base so as to allow the ambient atmosphere to pass between the edges of the base and cover and about the well walls and into the wells over their upper edges. This arrangement is explained in detail in the following description.

The base 10 and the cover 12 are both made of a transparent plastic material such as styrene and both are made by the injection molding process. The base 10 includes a planar, rectangular bottom wall 14 having a surrounding rim 16 that extends about the four sides of the bottom wall. Bottom wall 14 typically may be 0.040 inch in thickness and the mold from which the base is made is carefully machined so as to provide a very high degree of transparency for the bottom wall. A bead 18 is formed on the bottom wall 14 just inwardly of the rim 16, which bead 18 extends downwardly from the lower surface 20 of the bottom wall to provide a support for placing the base on a flat surface. The bead 18 is intended to elevate the lower surface 20 of the bottom wall off the base so that the lower surface will not become marred or dirty from the support on which the base is placed. Typically, the bead may also be 0.040 inch in height, and the rim 16 that surrounds the base may be approximately 0.185 inch measured from the lower surface of the bottom wall 14.

In the embodiment shown in FIGS. 1-7, the base 10 is provided with 12 separate wells 22 designed to receive the tissue culture or other material to be cultivated or otherwise investigated in the dish. Each well is formed by a cylindrical wall 24 that extends upwardly from the upper surface 26 of bottom wall 14, and the upper edges 25 of the cylindrical walls are coplanar and lie in a plane parallel to the bottom wall 14. The upper edges 25 of the wells are flat, and the walls themselves may be provided with a slight draft so as to facilitate molding. The wells measured from the upper surface 26 of bottom wall 14 which defines the bottom of the wells to the edges 25 may be approximately 0.70 inch.

The wells 22 are arranged in three rows of four wells each, and the wells are aligned so as to form mutually perpendicular rows across and lengthwise of the base. For strength and rigidity, braces 30 interconnect the outer surfaces of the adjacent wells at the points of closest proximity to one another, and the wells at the periphery of the base are strengthened by braces 32 between the side walls of the wells and the rim 16. Certain of the braces 32 are provided with shoulders 34 adjacent their bottom just above the upper edge 36 of rim 16, which shoulders support the lower edges of the cover when the cover is in the closed position shown in FIG. 2.

As shown in FIG. 7, at one end 40 of base 10 the wells 22a at the ends of the three rows are spaced a short distance from the peripheral wall 16, and vertical ribs 42 extend between the outside wells 22a and the rim 16. Each rib 42 is provided with a shoulder 44 (see FIGS. 5 and 5A) which supports the corresponding edge of the cover 12 when the cover is in the closed position of FIG. 5, and the ribs 42 are further notched as shown at 46 to form a seat for the edge of the cover when the cover is mounted in the tilted or partially open position of FIGS. 1, 3 and 5A. Notches 46 include a lower wall 48, an outer vertical wall 50 and is further defined by the outer surface 52 of the cylindrical wall of the well 22a (see FIG. 5A). The manner in which the notch 46 receives the edge of the cover is described below after the detailed description of the cover.

As described above, the various wells 22 all extend upwardly from the bottom wall 14 and therefore with the exception of the braces 30 and 32, the sides of the wells are fully exposed so that the contents of the wells may be visually examined. The top edges 25 of the wells all are positioned substantially above the upper surface of bottom wall 14. Consequently, if any reagent spills out of one well for any reason, the material will flow down the outside of the cylindrical walls to the upper surface of the bottom well 14, and it will not flow from one well into another, which could cause cross contamination. It will also be noted that the tops of the braces which join the walls of adjacent wells lie below the upper edges 25 so that they cannot serve as paths for the flow of material from one well to another.

Cover 12 includes a top flat closure wall 60 and a peripheral skirt 62 that extends about the four sides of the top wall. Along the two long sides and the front end of the cover, the skirt 62 is substantially vertical except that it may be provided with a slight draft to facilitate molding. At the rear end of the cover, the skirt 62 is inclined as shown at 64 in FIGS. 1, 3, 5 and 5a. The outer surface of the inclined portion 64 may be textured or otherwise treated to enable the user to write on the surface.

The lower edge 66 of the skirt is coplanar about the four sides of the cover, and the lower edge 66 is designed to sit on the shoulders 34 and 44 of the braces and ribs when the cover is mounted in the closed position. It will be noted in FIGS. 2-5 that when the cover is mounted in the closed position on those shoulders, a gap 68 is provided to allow the interior of the dish to communicate with the ambient atmosphere. In that position, the bottom surface 70 of top closure wall 60 is spaced above the rims 25 of the wells (see FIG. 4) so as to allow that same communication to extend to the interior of the wells.

Extending slightly downwardly from the lower surface 70 of cover 12 are circular flanges 72 which, when the cover is in place on the base, extend around the outsides of the upper edges 25 of the well walls. The lower extremities of the flanges 72 lie in a horizontal plane lower than the edges 25 of the wells, but the flanges do not contact the outsides of the cylindrical well walls and therefore do not interfere with atmospheric communication between the interior of the wells even when the cover is in place. The flanges 72 do, however, reduce the possibility of cross contamination as they will prevent condensate or other material above one well on the lower surface of the cover from creeping on the lower surface 70 and subsequently dropping into another well.

The width of the inclined section 64 of skirt 62 is greater than the distance between the notches 46 in the ribs 42. The thickness of the skirt section 64 is approximately 0.040 inch, and therefore the cover may be mounted on the base with the bottom edge 76 of the skirt section 64 within the notches 46. This is clearly shown in FIGS. 3 and 5a.

Figure 3:
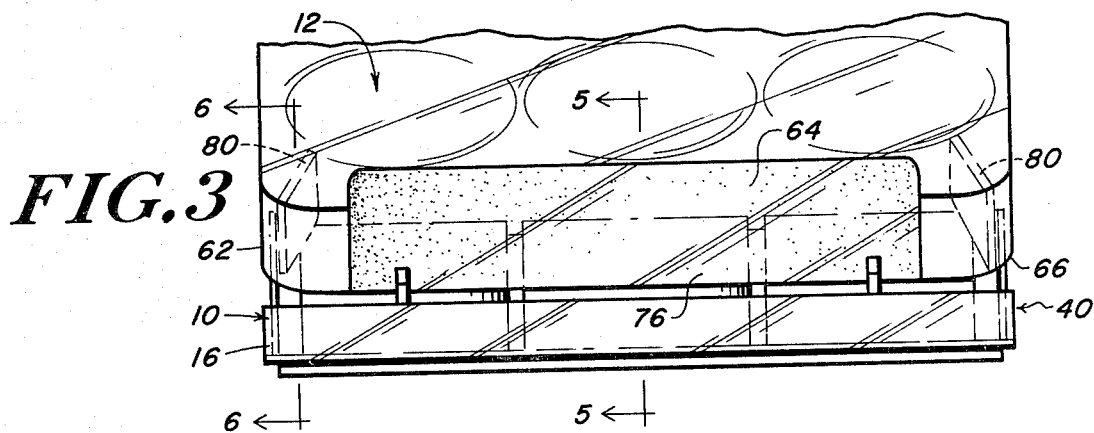
FIG. 3 is a rear end elevation view of the dish with the cover in the partially open position of FIG. 1.

A pair of stops 80 are formed in the rear corners of the cover as shown in FIGS. 3 and 6, and these stops are so shaped that their edges 82 bear against the cylindrical wall 52 of the two outside wells 22a when the cover is mounted in the tilted or partially open position so as to maintain the cover in that position when the skirt 64 is placed in the slots 46. Thus, the slots 46 with the skirt section 64 cooperate with the stops 80 so as to enable the investigator to mount the cover in the partially open position as shown. The stops 80, of course, do not interfere with the placement of the cover in the closed position of FIGS. 2, 4 and 5, as they lie outside the flanges 72 in the cover and outside the wells on the base. It will be appreciated that when mounted in the tilted position the cover will remain in that position, and the assembly may be carried in one hand without separate hand support for the cover.

A second pair of stops 84 are formed as an integral part of the base 10 and extend diagonally from the walls of the outside wells 22a to the rim 16. The stops 84 have outer edges 86 which lie immediately adjacent the inner surface of the skirt 62 of the cover when the cover is mounted in the partially open position so as to prevent the cover from moving from side to side in the slots 46. The edges 86 of the stops 84 also lie just within the inner surface of the skirt 62 when the cover is in the fully closed position so as to prevent the cover from sliding sideways on the base. The braces 32 similarly serve to stabilize the cover on the base when the cover is in the closed position.

Figure 8:
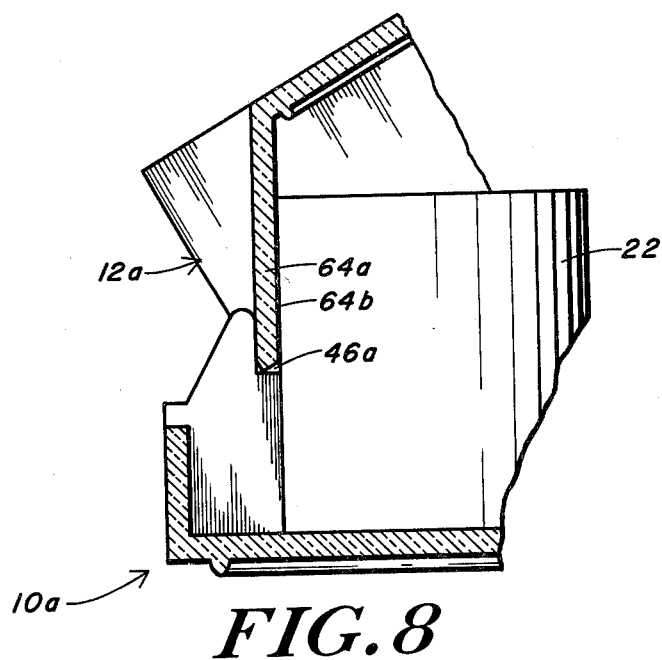
FIG. 8 is a view similar to FIG. 5A but showing a second embodiment of the invention.

In the embodiment of FIG. 8, a slightly different arrangement is shown for supporting the cover 12a in the partially open or tilted position on base 10a. In that embodiment the notch 46a is shown to be smaller than the notch 46 in the embodiment of FIGS. 1-7. The width of notch 46a just exceeds the thickness of the inclined portion 64a of the skirt of the cover. Consequently, when the cover is mounted in the inclined position, the inner surface 64b of the inclined portion of the skirt bears against the outer surfaces of the wells 22 so as to eliminate the need for the stops 80 shown in the first embodiment. The depth of notch 46a is somewhat increased to form a firm support for the cover.

It will be appreciated that the culture cluster dish of this invention has many advantages. First, it is very convenient to use because of the ability to mount the cover on the base in the partially open position. The monoplane surface of the base provides maximum optical clarity because of the manner in which the mold for manufacturing it may be gated. The sides of the wells are not surrounded by other walls on the base which would interfere with the viewing of the well contents. And the separation between the wells prevents flow from one well to another. Other advantages are derived from the device as well.

Having described this invention in detail, those skilled in the art will appreciate that numerous modifications may be made of this invention without departing from its spirit. Therefore, it is not intended to limit the breadth of this invention to the embodiments illustrated and described. Rather, it is intended that the breadth of this invention be determined by the appended claims and their equivalents.

We claim:

1. A tissue culture cluster dish comprising
    a base having a plurality of wells joined in a unitary structure for receiving materials, said wells having closed bottoms and upstanding side walls,
    a rim structure forming the periphery of the base for supporting the base on a surface with the bottom of the wells raised above said surface,
    a cover having a top closure wall and a peripheral skirt, said cover being adapted to be supported in a first position with the closure wall spaced just above the top edges of the side walls of the wells to permit the interior of the wells to be exposed to the ambient atmosphere,
    and support means formed as part of the base for engaging the skirt of the cover for supporting the cover on the base in a second position wherein the cover is lifted at an angle with respect to the base to permit access to the wells by a pipette or other instrument while preventing contamination of the wells by airborne substances.

2. A tissue culture cluster dish as defined in claim 1 further characterized by
    means defining notches formed in the base at one end thereof for receiving the skirt of the cover,
    and means on the cover and base cooperating with one another when the side wall of the cover is in the notches for holding the cover in said second position.

3. A tissue culture cluster dish as defined in claim 2 further characterized by
    said means on the cover being stops which engage certain of the wells.

4. A tissue culture cluster dish as defined in claim 2 further characterized by
    said wells being arranged in rows at right angles to one another,
    said means defining the notches including ribs connected between certain of the wells at the ends of the rows and the rim structure of the of the base with the notches being formed in the ribs.

5. A tissue culture cluster dish as defined in claim 4 further characterized by
    said cover skirt having an inclined section which slopes upwardly and inwardly from its bottom to the top closure wall, said inclined section fitting into the notches when the cover is supported in the second position.

6. A tissue culture cluster dish as defined in claim 5 further characterized by
    said inclined section of the skirt being textured to enable the user to write on the section.

7. A tissue culture cluster dish as defined in claim 6 further characterized by
    said base having a solid and continuous bottom wall, said wall defining the bottoms of the wells,
    and said side walls of the wells extending upwardly from the bottom wall,
    and said rim structure of the base permitting direct viewing of the sides of the wells without looking through the rim structure.

8. A tissue culture cluster dish as defined in claim 1 further characterized by
    said base having a solid and continuous bottom wall, said wall defining the bottoms of the wells,
    and said side walls of the wells extending upwardly from the bottom wall,
    and said rim structure of the base permitting direct viewing of the sides of the wells without looking through the rim structure.

9. A tissue culture cluster dish as defined in claim 1 further characterized by
    means defining notches formed in the base at one end thereof for receiving the skirt of the cover,
    portions of said skirt engaging the side walls of certain of the wells and cooperating with the notches to hold the cover in the second position.

10. A tissue culture cluster dish as defined in claim 1 further characterized by
    means defining notches formed in the base at one end thereof for receiving the skirt of the cover,
    said cover skirt having an inclined section which slopes upwardly and inwardly from its bottom to the top closure wall, said inclined section fitting into the notches when the cover is supported in the second position.

* * * * *